United States Patent [19]

Chekroun et al.

[11] Patent Number: 5,382,672
[45] Date of Patent: Jan. 17, 1995

[54] PREPARATION OF DERIVATIVES OF BENZENEBORINIC ACID

[75] Inventors: Isaac Chekroun, Epinay; José Ruiz-Montes, Mantes-la-Jolie; Manuel Bedoya-Zurita, Paris; Guy Rossey, Voisins-le-Bretonneux, all of France

[73] Assignee: Synthelabo, Le Plessis Robinson, France

[21] Appl. No.: 155,170

[22] Filed: Nov. 19, 1993

Related U.S. Application Data

[62] Division of Ser. No. 967,908, Oct. 29, 1992, Pat. No. 5,278,312.

[30] Foreign Application Priority Data

Oct. 12, 1992 [FR] France ................................ 92 12166

[51] Int. Cl.$^6$ ............................................. C07D 257/04
[52] U.S. Cl. ..................................... 548/110; 558/288; 568/6
[58] Field of Search ......................... 548/110; 558/288; 568/6

[56] References Cited

U.S. PATENT DOCUMENTS 5,130,439  7/1992  Lo et al. ............................... 548/110

FOREIGN PATENT DOCUMENTS 297637  12/1990  German Dem. Rep. .

OTHER PUBLICATIONS

Chemical Abstracts, vol. 104, No. 23, Abstract 207334 (1986).

*Primary Examiner*—Joseph Paul Brust
*Assistant Examiner*—Mary Susan H. Gabilan
*Attorney, Agent, or Firm*—Jacobson, Price, Holman & Stern

[57] ABSTRACT

Derivatives of benzeneborinic acid, preparation thereof and use thereof as synthetic intermediates.

1 Claim, No Drawings

PREPARATION OF DERIVATIVES OF BENZENEBORINIC ACID

This is a divisional application of application Ser. No. 07/967,908, filed Oct. 29, 1992, now U.S. Pat. No. 5,278,312.

The present invention relates to derivatives of benzeneborinic acid corresponding to the formula (1)

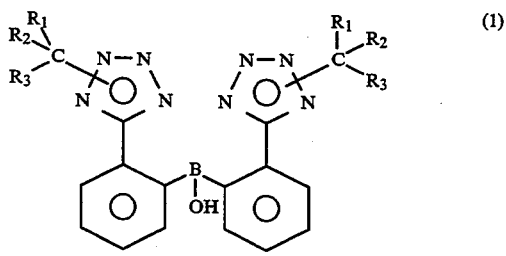

in which $R_1$, $R_2$ and $R_3$ represent, each independently of the others, either a $(C_1-C_2)$alkyl group or an aryl group, the group $-CR_1R_2R_3$ being in position 1 or 2 of the tetrazole ring, to their preparation and to their use in aryl-aryl, aryl-naphthyl or aryl-heterocycle couplings in the presence of palladium catalysts.

The preferred compounds according to the invention are the compounds corresponding to the formula (1) in which the group $-CR_1R_2R_3$ is the 1,1-dimethylethyl group.

The compounds of the invention can be prepared, from 2-(1,1-dimethylethyl)-5-phenyltetrazole, in the following way: 2-(1,1-dimethylethyl)-5-phenyltetrazole is reacted with an alkyllithium, such as butyllithium, in an aprotic solvent such as tetrahydrofuran at a temperature between $-50°$ C. and $+66°$ C. An organolithium compound is obtained which is reacted with trialkyl borate in a solvent such as tetrahydrofuran. An alkyl benzeneborinate is obtained which is subjected to a hydrolysis reaction.

In a variant of the process, an organomagnesium compound is prepared from a halogenated derivative of 2-(1,1-dimethylethyl)-5-phenyltetrazole and then the preparation is continued as described above.

The starting compounds are commercially available or are described in the literature or can be prepared according to methods which are described therein or which are known to those skilled in the art.

Thus, 2-(1,1-dimethylethyl)-5-phenyltetrazole is prepared according to the method described for an analogous derivative by J. W. Tilley et al., J. Med. Chem. 1991, 34, 1125–1126.

The derivatives of benzeneborinic acid thus obtained are stable solids which can be coupled with aromatic or heterocyclic halides containing numerous substituents, such as, for example, carboxamide, carbonyl, carboxyl, cyano, alkoxy or nitro groups. These couplings can be carried out in aqueous/organic medium.

The 1,1-dimethylethyl group is a protecting group which is particularly stable under various reaction conditions encountered in organic chemistry. Its use as a protecting group for the tetrazolyl functional group allows the compounds of the invention and the products resulting therefrom to be used in various chemical conversion reactions.

The examples which follow illustrate the preparation of the compounds according to the invention in detail.

Microanalysis and IR and NMR spectra confirm the structures of the compounds obtained.

EXAMPLE

Bis[2-[2-(1,1-dimethylethyl)-2H-tetrazol-5-yl]phenyl]borinic acid.

Organolithium Route 50g (0.247 mol) of 2-(1,1-dimethylethyl)-5-phenyl-2H-tetrazole and 200 ml of anhydrous tetrahydrofuran are introduced into a 1 liter, three-necked, round-bottom flask under nitrogen. The solution is allowed to cool and 150 ml of a 2.5 M solution of n-butyllithium in hexane are added dropwise. The mixture is stirred for 30 minutes at room temperature and then for 30 minutes at 50° C. The reaction mixture is cooled to 0° C. and a solution of 17 ml (0.148 mol) of trimethyl borate in 100 ml of anhydrous tetrahydrofuran is added while maintaining the temperature at 0° C. The mixture is left stirring overnight at room temperature and is then poured onto 250 ml of a 10% hydrochloric acid solution. The mixture is extracted with 500 ml of ethyl acetate, the organic phase is collected, washed with 100 ml of water and dried over magnesium sulfate. After filtering and evaporating the solvents, the product is crystallized from isopropyl ether. 24.3 g of product are obtained. Melting point=157°–159° C. Yield=45%

Organomagnesium Route 0.37 g (15 mmol) of magnesium turnings are introduced, under nitrogen, into 5 ml of anhydrous tetrahydrofuran in a 100 ml, three-necked, round-bottom flask equipped with a condenser. 3.28 g (10 mmol) of 2-(1,1-dimethylethyl)-5-(2-iodophenyl)-2H-tetrazole in 20 ml of anhydrous tetrahydrofuran are then added dropwise while maintaining a gentle reflux. The solution is stirred for 30 minutes at 50° C. and is then allowed to return to room temperature. 2.3 ml (20 mmol) of trimethyl borate in 15 ml of anhydrous tetrahydrofuran are then added dropwise to this solution. The mixture is left stirring overnight at room temperature and is then poured onto 50 ml of a 10% hydrochloric acid solution. The mixture is extracted with 100 ml of ethyl acetate, the organic phase is collected, washed with 30 ml of water and dried over magnesium sulfate. After filtering and evaporating the solvents, the residue obtained is purified by chromatography on a silica gel column. 1.4 g of product is obtained. Melting point =157°–159° C. Yield=65%

The compounds according to the invention can be used for the synthesis of compounds corresponding to the formula (I)

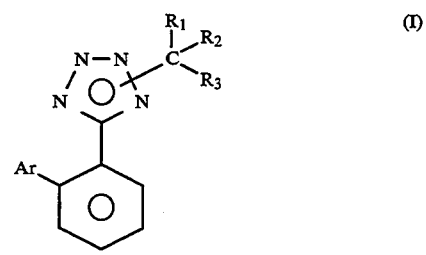

in which Ar represents either an optionally substituted aryl group, or an optionally substituted naphthyl group, or a heterocycle chosen from the optionally substituted pyridyl, pyrimidinyl, thienyl, imidazolyl, quinolyl and imidazopyridyl groups and $R_1$, $R_2$ and $R_3$ are as defined above.

A derivative of benzeneborinic acid of general formula (1) is reacted with a derivative of general formula Ar-Z, in which Z is a halogen atom and Ar is as defined above, in the presence of a base, such as, for example, sodium carbonate, potassium carbonate, potassium dihydrogenphosphate or a tertiary amine such as triethylamine, and of a catalyst, such as tetrakis(triphenylphosphine)palladium, in a solvent, such as, for example, toluene, benzene, xylene, dimethylformamide or an ether such as 1,2-dimethoxyethane.

The examples below illustrate the synthesis of the compounds of general formula (I) from the compounds according to the invention.

A 6-butyl -2-(2-phenylethyl)-5-[[2'[2-(1,1-dimethylethyl) -2H-tetrazol-5-yl][1,1'-biphenyl]-4-yl]methyl]-pyrimidin -4(3H)one [sic]

10.1 g (23.5 mmol) of bis[2-[2-(1,1-dimethylethyl) -2H-tetrazol-5-yl]phenyl]borinic acid, 20 g (47 mmol) of 5-[(4-bromophenyl)methyl]-6-butyl-2-(2-phenylethyl)-pyrimidin-4(3H)one [sic], 1.63 g (1.41 mmol) of tetrakis(triphenylphosphine)palladium, 47 ml of a 2 M [sic]sodium carbonate solution and 200 ml of toluene are introduced successively into a two-necked, round-bottom flask equipped with a condenser. This mixture is maintained at reflux temperature for 16 hours. After cooling and settling, the aqueous phase is collected and is extracted with 300 ml of ethyl acetate. The organic phases are combined and are washed successively with 100 ml of water and 200 ml of a saturated sodium chloride solution. The combined organic phases are dried over magnesium sulfate, the solvents are evaporated and the residue is purified by chromatography on a silica gel column. 15.7 g of product are obtained in the form of a white solid. Melting point=143°-145° C. Yield=61%

B 2'[2-(1,1-dimethylethyl)-2H-tetrazol -5-yl][1,1'-biphenyl]-4-carboxaldehyde [sic]

9.2 g (21.3 mmol) of bis[2-[2-(1,1-dimethylethyl) -2H-tetrazol-5-yl]phenyl]borinic acid, 5 g (35.5 mmol) of 4-chlorobenzaldehyde, 2.05 g of tetrakis(triphenylphosphine)palladium, 36 ml of a 2 M [sic]sodium carbonate solution and 150 ml of toluene are introduced into a 500 ml, round-bottom flask equipped with a condenser. The reaction mixture is maintained at reflux for 6 hours and is then poured into 50 ml of a saturated ammonium chloride solution. The mixture is extracted with ethyl acetate, the organic phase is collected and is washed successively with 100 ml of water and 100 ml of a saturated sodium chloride solution. The organic phase is dried over magnesium sulfate and is evaporated under vacuum. The residue obtained is purified by chromatography on a silica gel column. 7.06 g of product are obtained. Melting point=71°-73° C. Yield=65%

C 2-(1,1-dimethylethyl)-5-[2-(naphthalen-1-yl)phenyl]- 2H-tetrazole 4 g (9.3 mmol) of bis[2-[2-(1,1-dimethylethyl) -2H-tetrazol-5-yl]phenyl]borinic acid, 2.4 ml (16.7 mmol) of 1-bromonaphthalene, 0.98 g of tetrakis(triphenylphosphine)palladium, 17 ml of a 2 M [sic]sodium carbonate solution and 50 ml of toluene are introduced into a three-necked, round-bottom flask equipped with a condenser. The reaction mixture is maintained at reflux for 10 hours and is then poured into 50 ml of a saturated sodium chloride solution. The mixture is extracted with ethyl acetate, the organic phase is collected and is washed successively with 100 ml of water and 100 ml of a saturated sodium chloride solution. The organic phase is dried over magnesium sulfate and is evaporated under vacuum. The residue obtained is purified by chromatography on a silica gel column. 3.6 g of product are obtained. Melting point=83°-85° C. Yield=65%

The process according to the invention makes it possible to obtain compounds of formula (I) in high purity and with a good yield.

It allows coupling to take place of aromatic or heterocyclic halides containing common organic functional groups such as, for example, alcohols, ethers, amines, aldehydes, ketones, acids, esters, nitriles, amides, and nitrated or sulfur-containing derivatives.

Moreover, this process avoids the use of explosive azides and contributes to the protection of the environment (recycling of palladium).

We claim:

1. Process for the preparation of bis[2-[2-(1,1-dimethylethyl)-2H-tetrazol-5-yl]phenyl]borinic acid, which process comprises reacting 2-(1,1-dimethylethyl)-5-phenyltetrazole with an alkyllithium in an aproptic solvent at a temperature between −50° C. and +66° C. to obtain an organolithium compound, reacting said organolithium compound with trialkyl borate in an aproptic solvent to obtain an alkyl benzeneborinate and hydrolyzing said alkyl benzeneborinate.

* * * * *